(12) United States Patent
Kempson et al.

(10) Patent No.: US 7,109,224 B2
(45) Date of Patent: Sep. 19, 2006

(54) ACYL GUANIDINE COMPOUNDS AND USE THEREOF

(75) Inventors: James Kempson, Princeton, NJ (US); William J. Pitts, Newtown, PA (US)

(73) Assignee: Bristol-Myers Squibb Co., Princeton, NJ (US)

( * ) Notice: Subject to any disclaimer, the term of this patent is extended or adjusted under 35 U.S.C. 154(b) by 201 days.

(21) Appl. No.: 10/702,934

(22) Filed: Nov. 6, 2003

(65) Prior Publication Data

US 2004/0132750 A1 Jul. 8, 2004

Related U.S. Application Data

(60) Provisional application No. 60/424,237, filed on Nov. 6, 2002.

(51) Int. Cl.
| | | |
|---|---|---|
| C07D 263/30 | (2006.01) | |
| C07D 277/20 | (2006.01) | |
| A61K 31/155 | (2006.01) | |
| A61K 31/421 | (2006.01) | |
| A61K 31/427 | (2006.01) | |
| A61P 19/02 | (2006.01) | |

(52) U.S. Cl. ................. 514/370; 514/377; 548/190; 548/233

(58) Field of Classification Search ................ 548/190, 548/233; 514/370, 377
See application file for complete search history.

(56) References Cited

U.S. PATENT DOCUMENTS

| | | | |
|---|---|---|---|
| 4,246,406 A | 1/1981 | Cragoe, Jr. et al. | |
| 4,933,355 A | 6/1990 | Yoshioka et al. | |
| 5,185,334 A | 2/1993 | Solomon et al. | |
| 5,308,857 A | 5/1994 | Takasugi et al. | |
| 5,449,680 A | 9/1995 | Solomon et al. | |
| 5,527,896 A | 6/1996 | Wigler et al. | |
| 5,977,305 A | 11/1999 | Wigler et al. | |
| 6,297,233 B1 | 10/2001 | Stein et al. | |

FOREIGN PATENT DOCUMENTS

JP 6-138504 5/1994

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Cecil Textbook of Medicine, edited by Bennet, J.C., and Plum F., 20th edition,vol. 1, 1004-1010, 1996.*
Goronzy et al., Curr. Opin.. Rheumatol. 16(3)212-217, 2004.*
Dorner et al., Curr. Opin.. Rheumatol. 16(3)246-263, 2004.*
Beyer, H. et al., "Über Thiazole XL: Synthesen von Thiazolyl-(2)-guanidinen", Chemische Berichte, vol. 95, pp. 893-901 (1962).
Fahmy, S.M. et al., "Reactions with Heterocyclic Amidines, X: Synthesis of Some New Azolylthiourea Derivatives", Arch. Pharm. (Weinheim), vol. 315, pp. 791-797 (1982).
Fahmy, S.M. et al., "Reactions with Heterocyclic Amidines, X: Synthesis of Some New Azolylthiourea Derivatives", Iraqi J. Sci., vol. 23, No. 1, pp. 28-41 (1982).
Han, P. et al., "Alternative Splicing of the High Affinity cAMP-Specific Phosphodiesterase (PDE7A) mRNA in Human Skeletal Muscle and Heart", The Journal of Biological Chemistry, vol. 272, No. 26, pp. 16152-16157 (1997).
Henry, J.R. et al., "p38 mitogen-activated protein kinase as a target for drug discovery", Drugs of the Future, vol. 24, No. 12, pp. 1345-1354 (1999).
Hurst, D.T. et al., "The Synthesis of Some Pyrimidinyl and Thiazolyl Ureas and Thioureas and Some Related Compounds", Aust. J. Chem., vol. 41, pp. 1221-1229 (1988).
Li, L. et al., "CD3- and CD28-Dependent Induction of PDE7 Required for T Cell Activation", Science, vol. 283, pp. 848-851 (1999).
Moreland, L.W. et al., "Etanercept Therapy in Rheumatoid Arthritis: A Randomized, Controlled Trial", Ann. Intern. Med., vol. 130, pp. 478-486 (1999).
Nakata, A. et al., "Potential role of phosphodiesterase 7 in human T cell function: comparative effects of two phosphodiesterase inhibitors", Clin. Exp. Immunol., vol. 128, pp. 460-466 (2002).
Rankin, E.C.C. et al., "The Therapeutic Effects of an Engineered Human Anti-Tumor Necrosis Factor Alpha Antibody (CDP571) in Rheumatoid Arthritis", British Journal of Rheumatology, vol. 34, pp. 334-342 (1995).
Salituro, F.G. et al., "Inhibitors of p38 MAP Kinase: Therapeutic Intervention in Cytokine-Mediated Diseases", Current Medicinal Chemistry, vol. 6, pp. 807-823 (1999).
Sasaki, T. et al., "Identification of Human PDE7B, a cAMP-Specific Phosphodiesterase", Biochemical and Biophysical Research Communications, vol. 271, pp. 575-583 (2000).

* cited by examiner

Primary Examiner—Venkataraman Balasubramanian
(74) Attorney, Agent, or Firm—Laurelee A. Duncan

(57) ABSTRACT

Acyl guanidine compounds of the following Formula

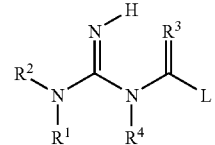

wherein $R^1$, $R^2$, $R^3$, $R^4$ and L are described herein, and pharmaceutical compositions thereof, are useful in treating leukocyte activation-associated disorders.

16 Claims, No Drawings

ACYL GUANIDINE COMPOUNDS AND USE THEREOF

This application claims priority from U.S. provisional application Ser. No. 60/424,237 filed Nov. 6, 2002, the entirely of which is incorporated herein by reference.

FIELD OF THE INVENTION

The present invention relates to acyl guanidine compounds, pharmaceutical compositions containing these compounds, and the use of these compounds in the treatment of leukocyte activation-associated disorders.

BACKGROUND OF THE INVENTION

The immune system plays an important role in host defense. In the treatment of leukocyte activation-associated disorders is often desirable to attenuate the immune response. Such disorders include the immune response incurred by transplantation or diseases improved by decreased T-cell activation and proliferation. It is accepted that agents that inhibit T-cell proliferation may be useful in the treatment of the aforementioned disorders.

A number of agents demonstrate clinical or therapeutic utility by attenuating or modulating the immune system. Such agents include Cyclosporin A ("CsA"), azathioprine, tacrolimus, sirolimus and mycophenolate mofetil. However, these agents often demonstrate a relatively high incidence (25 to >50%) of multiple unique liabilities during clinical or therapeutic use. For example, CsA therapy is associated with nephrotoxicity, azathioprine therapy is associated with leukopenia, and tacrolimus therapy is associated with undesirable effects on the central nervous system. Also, sirolimus therapy is associated with hypertension, hyperlipidemia and hypercholesterolemia, and mycophenolate mofetil therapy is associated with diarrhea.

The overproduction of cytokines, such as TNF-α, is also implicated in a wide variety of leukocyte activation-associated disorders, including rheumatoid arthritis (RA), psoriasis, multiple sclerosis, inflammatory bowel disease, endotoxin shock, osteoporosis, Alzheimer's disease and congestive heart failure, among others. See e.g., Henry et al., *Drugs Fut.*, 24:1345–1354 (1999); Salituro et al., *Curr. Med. Chem.*, 6:807–823 (1999). There is convincing evidence in human patients that cytokine protein antagonists can provide treatment for these disorders. See e.g., Rankin et al., *Br. J. Rheumatol.*, 34:334–342 (1995) (monoclonal antibody to TNF-α—Enbrel®); and Moreland et al., *Ann. Intern. Med.*, 130:478–486 (1999) (soluble TNF-α receptor-Fc fusion protein—etanercept). Accordingly, it is accepted that agents demonstrating TNF-α inhibitory activity are useful for the treatment of leukocyte activation-associated disorders.

As none of the current treatments provide complete relief of symptoms and are often associated with various liabilities, new agents and improved methods for treating leukocyte activation-associated disorders are needed.

SUMMARY OF THE INVENTION

The present invention provides novel fused heterocyclic compounds of the following Formula (I), their enantiomers, diastereomers, and pharmaceutically acceptable salts, prodrugs and solvates thereof, for use in treating leukocyte activation-associated disorders,

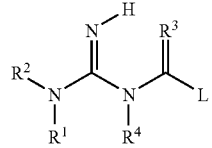

in which:

$R^1$ and $R^4$ are independently hydrogen or alkyl optionally independently substituted where valence allows with one to three groups, $T^1$, $T^2$ and/or $T^3$;

$R^2$ is

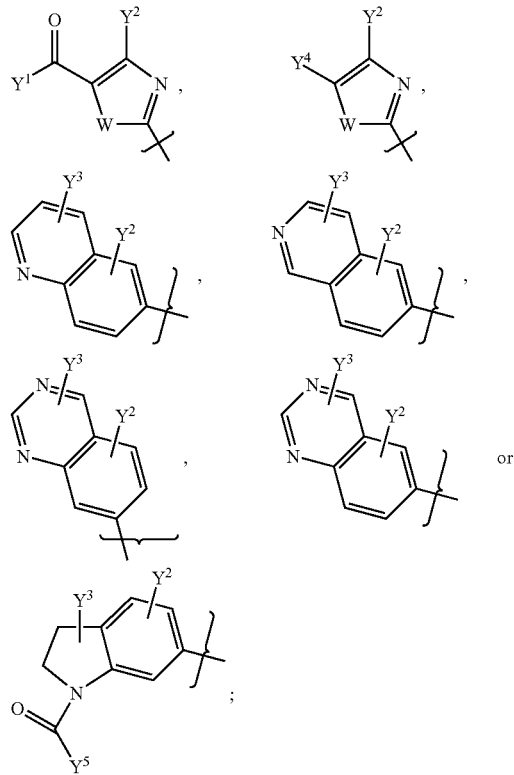

W is O or S;

$Y^1$ is —$NHT^{12}$ or $OT^7$;

$Y^2$ and $Y^3$ are independently hydrogen, halo, $OT^7$, alkyl or haloalkyl;

$Y^4$ is optionally substituted heteroaryl, cyano, $C(O)_tT^7$ or $S(O)_tNT^{11}T^{12}$; and $Y^5$ is alkyl, haloalkyl, $NHT^{12}$ or $OT^7$;

$R^3$ is O, S or N;

L is aryl, cycloalkyl, heterocyclo or heteroaryl, any of which is independently substituted where valence allows by one to three groups, $R^5$, $R^6$ and/or $R^7$;

$R^5$, $R^6$ and $R^7$ are independently (1) H, alkyl, halo, cyano, nitro, OH, $OR^{10}$, oxo, SH, aryl, cycloalkyl, heterocyclo or heteroaryl, any of which is optionally independently substituted where valence allows with one to three groups $T^4$, $T^5$ and/or $T^6$, provided that when L is aryl or heteroaryl none of $R^5$, $R^6$ and $R^7$ are oxo; or (2) $N(R^8)(R^9)$, —$C(O)N(R^8)(R^9)$, $S(O)_t$ $N(R^8)(R^9)$, —$S(O)_tR^{10}$ or $C(O)_tR^{10}$;

$R^8$ and $R^9$ are
  (1) independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which is optionally independently substituted where valance allows with one to three groups independently selected from $T^4$, $T^5$ and/or $T^6$; or
  (2) $R^8$ and $R^9$ may be taken together with the nitrogen atom to which they are attached to form a heterocyclo or heteroaryl ring, either of which is optionally independently substituted where valance allows with one to three groups independently selected from $T^4$, $T^5$ and/or $T^6$;

$R^{10}$ is H, alkyl or substituted alkyl;

$T^1$–$T^3$ are each independently halo, cyano, nitro, OH, oxo, —$OT^7$, —SH, —$ST^7$, amino, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl;

$T^4$–$T^6$ are each independently
  (1) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, any of which may be optionally independently substituted where valence allows by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —$OT^7$, —SH, —$ST^7$, —$C(O)_tH$, —$C(O)_tT^7$, —O—$C(O)T^7$, —$SO_3H$, —$S(O)_tT^7$, $S(O)_tN(T^8)T^7$, -$T^9$-$NT^{11}T^{12}$, -$T^9$-$N(T^8)$-$T^{10}$-$NT^{11}T^{12}$, -$T^9$-$N(T^{13})$-$T^{12}$-$T^7$ and -$T^9$-$N(T^{13})$-$T^{10}$-H; or
  (2) halo, cyano, nitro, OH, oxo, —$OT^7$, —SH, —$ST^7$, —$OT^7$, —SH, —$ST^7$, —$C(O)_tH$, —$C(O)_tT^7$, —O—$C(O)T^7$, —$SO_3H$, —$S(O)_tT^7$, $S(O)_tN(T^8)T^7$, -$T^9$-$NT^{11}T^{12}$, -$T^9$-$N(T^8)$-$T^{10}$-$NT^{11}T^{12}$, -$T^9$-$N(T^{13})$-$T^{12}$-$T^7$ or -$T^9$-$N(T^{13})$-$T^{10}$-H;

t is 1 or 2;

$T^7$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^9$ and $T^{10}$ are each independently a single bond, -$T^{14}$-$S(O)_t$-$T^{15}$-, -$T^{14}$-$C(O)$-$T^{15}$-, -$T^{14}$-$C(S)$-$T^{18}$-, -$T^{17}$-O-$T^{18}$-, -$T^{17}$-S-$T^{18}$-, -$T^{17}$-O—$C(O)$-$T^{18}$-, -$T^{17}$-$C(O)_tT^{18}$-, -$T^{17}$-C(=$NT^{16}$)-$T^{15}$- or -$T^{14}$-$C(O)$—$C(O)$-$T^{15}$-;

$T^8$, $T^{11}$, $T^{12}$, $T^{13}$ and $T^{16}$ are
  (1) independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —SH, —$ST^{19}$, —$C(O)_tH$, —$C(O)_tT^{19}$, —O—$C(O)T^{19}$ and —$S(O)_tT^{19}$; or
  (2) independently halo, cyano, nitro, OH, oxo, SH, —$ST^{19}$, —$C(O)_tH$, —$C(O)_tT^{19}$, —O—$C(O)T^{19}$ or —$S(O)_tT^{19}$; or
  (3) $T^{11}$ and $T^{12}$ may together be alkylene or alkenylene, completing a 3- to 8-membered saturated or unsaturated ring together with the atoms to which they are attached, which ring is substituted with one or more groups listed in the description of $T^{17}$; or
  (4) $T^{11}$ or $T^{12}$, together with $T^8$, may be alkylene or alkenylene completing a 3- to 8-membered saturated or unsaturated ring together with the nitrogen atoms to which they are attached, which ring is substituted with one or more groups independently selected from $T^{17}$; or
  (5) $T^{11}$ and $T^{12}$ or $T^8$ and $T^{13}$ together with the nitrogen atom to which they are attached may combine to form a group —N=$CT^{17}T^{18}$;

$T^{14}$ and $T^{15}$ are each independently a single bond, alkylene, alkenylene or alkynylene;

$T^{17}$ and $T^{18}$ are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —SH, —$ST^{19}$, —$C(O)_tH$, —$C(O)_tT^{19}$, —O—$C(O)T^{19}$ and —$S(O)_tT^{19}$; and $T^{19}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl.

DETAILED DESCRIPTION

The following are definitions of the terms as used throughout this specification and claims. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred.

The term "substituted alkyl" refers to alkyl groups substituted with one or more groups listed in the definition of $T^4$–$T^6$, preferably selected from halo (e.g. halo substituted alkyl [or "haloalkyl"] may be $CHF_2$, $CH_2F$, or $CF_3$), cyano, O—$R_{11}$, S—$R_{11}$, $NR_{12}R_{13}$, nitro, cycloalkyl, substituted cycloalkyl, oxo, aryl, substituted aryl, heterocyclo, heteroaryl, $CO_2R_{11}$, $S(O)R_{11}$, $SO_2R_{11}$, $SO_3R_{11}$, $SO_2NR_{12}R_{13}$, $C(O)NR_{12}R_{13}$, C(O)alkyl and C(O)H.

The term "alkylene" refers to a straight chain bridge of 1 to 4 carbon atoms connected by single bonds (e.g., —$(CH_2)_x$— wherein x is 1 to 5), which may be substituted with one or more groups listed in the definition of $T^4$–$T^6$.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl.

The term "substituted alkenyl" refers to an alkenyl group as defined above substituted with one or more groups listed in the definition of $T^4$–$T^6$, preferably selected from halo, cyano, O—$R_{11}$, S—$R_{11}$, $NR_{12}R_{13}$, nitro, cycloalkyl, substituted cycloalkyl, oxo, aryl, substituted aryl, heterocyclo, heteroaryl, $CO_2R_{11}$, $S(O)R_{11}$, $SO_2R_{11}$, $SO_3R_{11}$, $SO_2NR_{12}R_{13}$, $C(O)NR_{12}R_{13}$, C(O)alkyl and C(O)H.

The term "alkynyl" refers to straight or branched chain hydrocarbon group having 2 to 12 carbon atoms and one, two or three triple bonds, preferably 2 to 6 carbon atoms and one triple bond.

The term "substituted alkynyl" refers to an alkynyl group as defined above substituted with one or more groups listed in the definition of $T^4$–$T^6$, preferably selected from halo, cyano, O—$R_{11}$, S—$R_{11}$, $NR_{12}R_{13}$, nitro, cycloalkyl, substituted cycloalkyl, oxo, aryl, substituted aryl, heterocyclo, heteroaryl, $CO_2R_{11}$, $S(O)R_{11}$, $SO_2R_{11}$, $SO_3R_{11}$, $SO_2NR_{12}R_{13}$, $C(O)NR_{12}R_{13}$, $C(O)_t$alkyl and C(O)H.

The term "amino" refers to a nitrogen atom substituted with three groups selected from hydrogen and alkyl (preferably lower alkyl) groups. Each alkyl group may be optionally substituted with one or more groups listed in the definition of $T^4$–$T^6$.

The term "carbonyl" refers to C=O, which may also be designated as C(O).

The group —$C(O)_tX$ refers to C=O where t is 1 and the structure

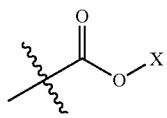

where t is 2.

The term "halo" or halogen refers to chloro, bromo, fluoro, and iodo.

The term "cycloalkyl" refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring and which may be fused to 1 or 2 aromatic or heterocyclo rings, which include cyclopropyl, cyclobutyl, cyclopentyl, cyclohexyl, cycloheptyl, cyclooctyl, cyclodecyl, cyclododecyl, cyclohexenyl,

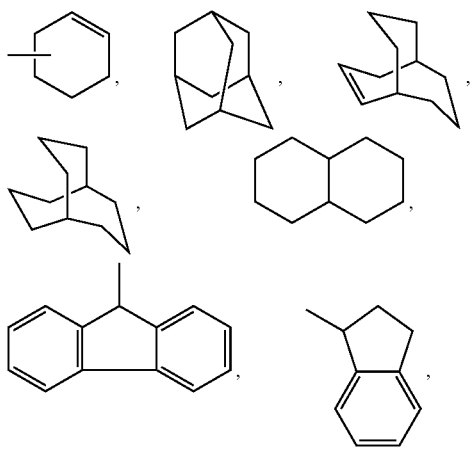

-continued

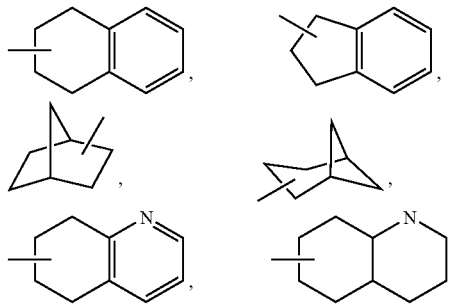

and the like.

The term "substituted cycloalkyl" refers to such cycloalkyl group as defined above substituted with one or more groups listed in the definition of $T^4$–$T^6$ preferably selected from halogen, nitro, alkyl, substituted alkyl, alkenyl, cyano, cycloalkyl, substituted cycloalkyl, aryl, substituted aryl, heterocyclo, heteroaryl, oxo, $OR_{11}$, $CO_2R_{11}$, $C(O)NR_{12}R_{13}$, $OC(O)R_{11}$, $OC(O)OR_{11}$, $OC(O)NR_{12}R_{13}$, $OCH_2CO_2R_{11}$, $C(O)R_{11}$, $NR_{12}R_{13}$, $NR_{14}C(O)R_{11}$, $NR_{14}C(O)OR_{11}$, $NR_{14}C(O)C(O)OR_{11}$, $NR_{14}C(O)C(O)NR_{12}R_{13}$, $NR_{14}C(O)C(O)$alkyl, $NR_{14}C(NCN)OR_{11}$, $NR_{14}C(O)NR_{12}R_{13}$, $NR_{14}C(NCN)NR_{12}R_{13}$, $NR_{14}C(NR_{15})NR_{12}R_{13}$, $NR_{14}SO_2NR_{12}R_{13}$, $NR_{14}SO_2R_{11}$, $SR_{11}$, $S(O)R_{11}$, $SO_2R_{11}$, $SO_3R_{11}$, $SO_2NR_{12}R_{13}$, $NHOR_{11}$, $NR_{14}NR_{12}R_{13}$, $N(COR_{11})OR_{14}$, $N(CO_2R_{11})OR_{14}$, $C(O)NR_{14}(CR_{16}R_{11})_rR_{11}$, $CO(CR_{16}R_{17})_pO(CR_{12}R_{13})_qCO_2R_{11}$, $CO(CR_{16}R_{17})_rOR_{11}$, $CO(CR_{16}R_{17})_pO(CR_{18}R_{13})_qR_{11}$, $CO(CR_{16}R_{17})_rNR_{12}R_{13}$, $OC(O)O(CR_{16}R_{17})_mNR_{12}R_{13}$, $OC(O)N(CR_{16}R_{17})_rR_{11}$, $O(CR_{16}R_{17})_mNR_{12}R_{13}$, $NR_{14}C(O)(CR_{16}R_{17})_rR_{11}$, $NR_{14}C(O)(CR_{16}R_{17})_rOR_{11}$, $NR_{14}C(=NC)(CR_{16}R_{17})_rR_{11}$, $NR_{14}CO(CR_{16}R_{17})_rNR_{12}R_{13}$, $NR_{14}(CR_{16}R_{17})_mOR_{11}$, $NR_{14}(CR_{16}R_{17})_rCO_2R_{11}$, $NR_{14}(CR_{16}R_{17})_mNR_{12}R_{13}$, $NR_{14}(CR_{16}R_{17})_nSO_2(CR_{18}R_{13})_qR_{11}$, $CONR_{14}(CR_{16}R_{17})_nSO_2(CR_{18}R_{13})_qR_{11}$, $SO_2NR_{14}(CR_{16}R_{17})_nCO(CR_{18}R_{19})_qR_{11}$ and $SO_2NR_{14}(CR_{16}R_{17})_mOR_{11}$.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl, as well as such rings fused to a cycloalkyl, cycloalkenyl, heterocyclo, or heteroaryl ring. Examples include:

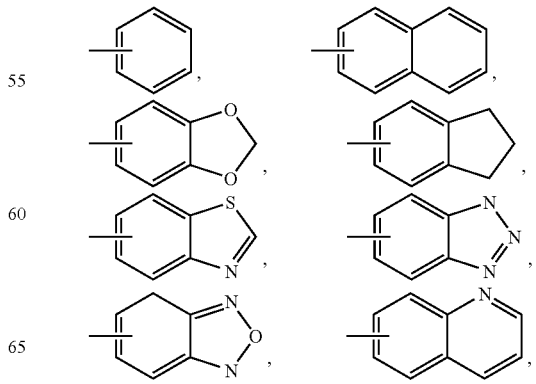

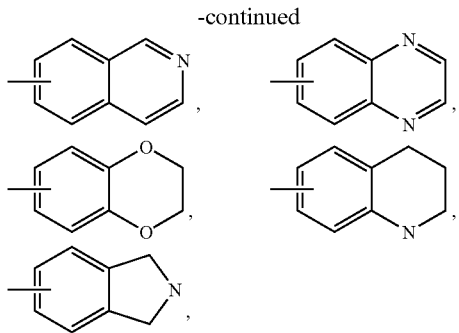

and the like.

The term "substituted aryl" refers to such aryl groups as defined above substituted with one or more groups listed in the definition of $T^4$–$T^6$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_{11}$, $CO_2R_{11}$, $C(O)NR_{12}R_{13}$, $OC(O)R_{11}$, $OC(O)OR_{11}$, $OC(O)NR_{12}R_{13}$, $OCH_2CO_2R_{11}$, $C(O)R_{11}$, $NR_{12}R_{13}$, $NR_{14}C(O)R_{11}$, $NR_{14}C(O)OR_{11}$, $NR_{14}C(O)C(O)OR_{11}$, $NR_{14}C(O)C(O)NR_{12}R_{13}$, $NR_{14}C(O)C(O)$alkyl, $NR_{14}C(NCN)OR_{11}$, $NR_{14}C(O)NR_{12}R_{13}$, $NR_{14}C(NCN)NR_{12}R_{13}$, $NR_{14}C(NR_{15})NR_{12}R_{13}$, $NR_{14}SO_2NR_{12}R_{13}$, $NR_{14}SO_2R_{11}$, $SR_{11}$, $S(O)R_{11}$, $SO_2R_{11}$, $SO_3R_{11}$, $SO_2NR_{12}R_{13}$, $NHOR_{11}$, $NR_{14}NR_{12}R_{13}$, $N(COR_{11})OR_{14}$, $N(CO_2R_{11})OR_{14}$, $C(O)NR_{14}(CR_{16}R_{17})_rR_{11}$, $CO(CR_{16}R_{17})_pO(CR_{12}R_{13})_qCO_2R_{11}$, $CO(CR_{16}R_{17})_rOR_{11}$, $CO(CR_{16}R_{17})_pO(CR_{18}R_{19})_qR_{11}$, $CO(CR_{16}R_{17})_rNR_{12}R_{13}$, $OC(O)O(CR_{16}R_{17})_mNR_{12}R_{13}$, $OC(O)N(CR_{16}R_{17})_rR_{11}$, $O(CR_{16}R_{17})_m$ $NR_{12}R_{13}$, $NR_{14}C(O)(CR_{16}R_{17})_rR_{11}$, $NR_{14}C(O)(CR_{16}R_{17})_r$ $OR_{11}$, $NR_{14}C(=NC)(CR_{16}R_{17})_rR_{11}$, $NR_{14}CO(CR_{16}R_{17})_r$ $NR_{12}R_{13}$, $NR_{14}(CR_{16}R_{17})_mOR_{11}$, $NR_{14}(CR_{16}R_{17})_rCO_2R_{11}$, $NR_{14}(CR_{16}R_{17})_mNR_{12}R_{13}$, $NR_{14}(CR_{16}R_{17})_nSO_2(CR_{18}R_{13})_qR_{11}$, $CONR_{14}(CR_{16}R_{17})_nSO_2(CR_{18}R_{19})_qR_{11}$, $SO_2NR_{14}(CR_{16}R_{17})_nCO(CR_{18}R_{19})_qR_{11}$ and $SO_2NR_{14}(CR_{16}R_{17})_mOR_{11}$ as well as pentafluorophenyl.

The terms "heterocycle", "heterocyclic", "heterocyclic group" or "heterocyclo" refer to fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions. Exemplary heterocyclic groups include

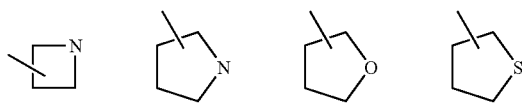

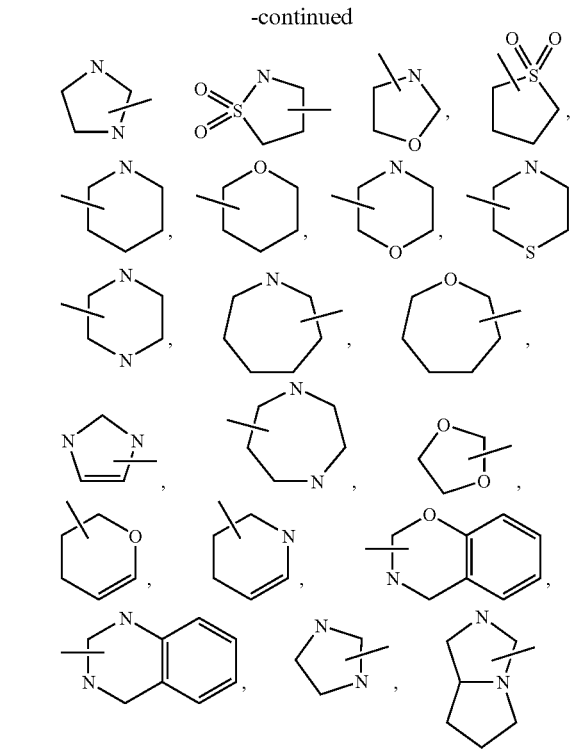

and the like.

The terms "substituted heterocycle" or "substituted heterocyclo" and the like refer to such heterocyclo groups as defined above substituted with one or more groups listed in the definition of $T^4$–$T^6$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_{11}$, $CO_2R_{11}$, $C(O)NR_{12}R_{13}$, $OC(O)R_{11}$, $OC(O)OR_{11}$, $OC(O)NR_{12}R_{13}$, $OCH_2CO_2R_{11}$, $C(O)R_{11}$, $NR_{12}R_{13}$, $NR_{14}C(O)R_{11}$, $NR_{14}C(O)OR_{11}$, $NR_{14}C(O)C(O)OR_{11}$, $NR_{14}C(O)C(O)NR_{12}R_{13}$, $NR_{14}C(O)C(O)$alkyl, $NR_{14}C(NCN)OR_{11}$, $NR_{14}C(O)NR_{12}R_{13}$, $NR_{14}C(NCN)NR_{12}R_{13}$, $NR_{14}C(NR_{15})NR_{12}R_{13}$, $NR_{14}SO_2NR_{12}R_{13}$, $NR_{14}SO_2R_{11}$, $SR_{11}$, $S(O)R_{11}$, $SO_2R_{11}$, $SO_3R_{11}$, $SO_2NR_{12}R_{13}$, $NHOR_{11}$, $NR_{14}NR_{12}R_{13}$, $N(COR_{11})OR_{14}$, $N(CO_2R_{11})OR_{14}$, $C(O)NR_{14}(CR_{16}R_{17})_rR_{11}$, $CO(CR_{16}R_{17})_pO(CR_{18}R_{13})_qCO_2R_{11}$, $CO(CR_{16}R_{17})_rOR_{11}$, $CO(CR_{16}R_{17})_pO(CR_{18}R_{19})_qR_{11}$, $CO(CR_{16}R_{17})_rNR_{12}R_{13}$, $OC(O)O(CR_{16}R_{17})_mNR_{12}R_{13}$, $OC(O)N(CR_{16}R_{17})_rR_{11}$, $O(CR_{16}R_{17})_m$ $NR_{12}R_{13}$, $NR_{14}C(O)(CR_{16}R_{17})_rR_{11}$, $NR_{14}C(O)(CR_{16}R_{17})_r$ $OR_{11}$, $NR_{14}C(=NC)(CR_{16}R_{17})_rR_{11}$, $NR_{14}CO(CR_{16}R_{17})_r$ $NR_{12}R_{13}$, $NR_{14}(CR_{16}R_{17})_mOR_{11}$, $NR_{14}(CR_{16}R_{17})_rCO_2R_{11}$, $NR_{14}(CR_{16}R_{17})_mNR_{12}R_{13}$, $NR_{14}(CR_{16}R_{17})_nSO_2(CR_{18}R_{13})_qR_{11}$, $CONR_{14}(CR_{16}R_{17})_nSO_2(CR_{18}R_{19})_qR_{11}$, $SO_2NR_{14}(CR_{16}R_{17})_nCO(CR_{18}R_{19})_qR_{11}$ and $SO_2NR_{14}(CR_{16}R_{17})_mOR_{11}$.

The term "heteroaryl" as used herein alone or as part of another group refers to a 5- 6- or 7-membered aromatic rings containing from 1 to 4 nitrogen atoms and/or 1 or 2 oxygen or sulfur atoms provided that the ring contains at least 1 carbon atom and no more than 4 heteroatoms. The heteroaryl ring is linked through an available carbon or nitrogen atom. Also included within the definition of heteroaryl are such rings fused to a cycloalkyl, aryl, cycloheteroalkyl, or another heteroaryl ring. One, two, or three available carbon or nitrogen atoms in the heteroaryl ring can be optionally substituted with substituents listed in the definition of $T^4$–$T^6$. Also an available nitrogen or sulfur atom in the heteroaryl ring can be oxidized. Examples of heteroaryl rings include

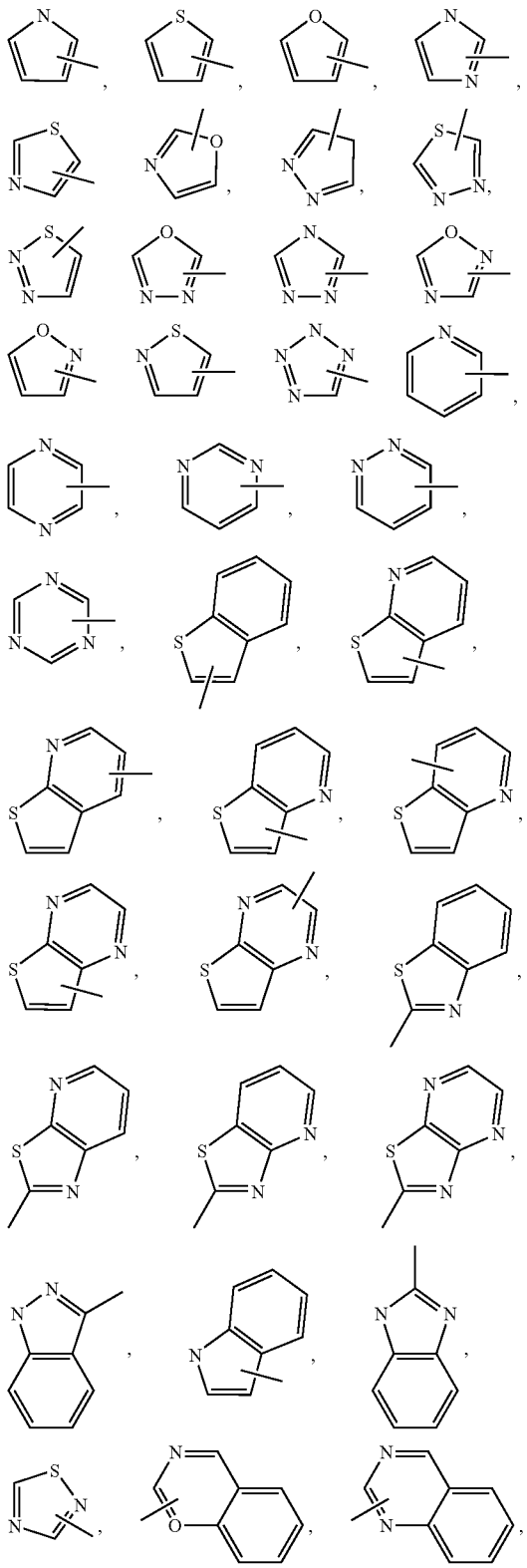

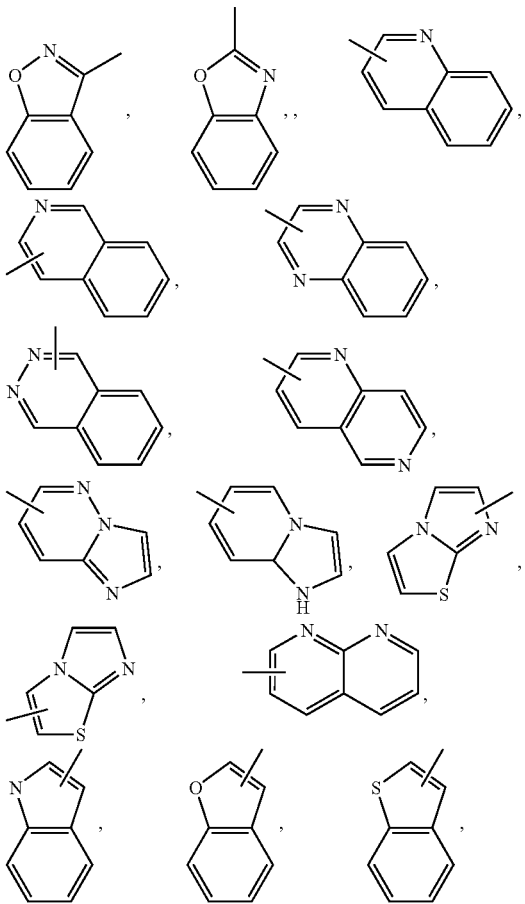

and the like.

The term "substituted heteroaryl" refers to such heteroaryl groups as defined above substituted on any available atom with one or more groups listed in the definition of $T^4$–$T^6$, "preferably selected from" refers to such heterocyclo groups as defined above substituted with one or more groups listed in the definition of $T^4$–$T^6$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_{11}$, $CO_2R_{11}$, $C(O)NR_{12}R_{13}$, $OC(O)R_{11}$, $OC(O)OR_{11}$, $OC(O)NR_{12}R_{13}$, $OCH_2CO_2R_{11}$, $C(O)R_{11}$, $NR_{12}R_{13}$, $NR_{14}C(O)R_{11}$, $NR_{14}C(O)OR_{11}$, $NR_{14}C(O)C(O)OR_{11}$, $NR_{14}C(O)C(O)NR_{12}R_{13}$, $NR_{14}C(O)C(O)alkyl$, $NR_{14}C(NCN)OR_{11}$, $NR_{14}C(O)NR_{12}R_{13}$, $NR_{14}C(NCN)NR_{12}R_{13}$, $NR_{14}C(NR_{15})NR_{12}R_{13}$, $NR_{14}SO_2NR_{12}R_{13}$, $NR_{14}SO_2R_{11}$, $SR_{11}$, $S(O)R_{11}$, $SO_2R_{11}$, $SO_3R_{11}$, $SO_2NR_{12}R_{13}$, $NHOR_{11}$, $NR_{14}NR_{12}R_{13}$, $N(COR_{11})OR_{14}$, $N(CO_2R_{11})OR_{14}$, $C(O)NR_{14}(CR_{16}R_{17})_rR_{11}$, $CO(CR_{16}R_{17})_p$ $O(CR_{12}R_{13})_qCO_2R_{11}$, $CO(CR_{16}R_7)_rOR_{11}$, $CO(CR_{16}R_{17})_p$ $O(CR_{18}R_{19})_qR_{11}$, $CO(CR_{16}R_{17})_rNR_{12}R_{13}$, $OC(O)O$ $(CR_{16}R_{17})_mNR_{12}R_{13}$, $OC(O)N(CR_{16}R_{17})_rR_{11}$, $O(CR_{16}R_{17})_m NR_{12}R_{13}$, $NR_{14}C(O)(CR_{16}R_{17})_rR_{11}$, $NR_{14}C(O)(CR_{16}R_{17})_r$ $OR_{11}$, $NR_{14}C(=NC)(CR_{16}R_{17})_rR_{11}$, $NR_{14}CO(CR_{16}R_{17})_r$ $NR_{12}R_{13}$, $NR_{14}(CR_{16}R_{17})_mOR_{11}$, $NR_{14}(CR_{16}R_{17})_r CO_2R_{11}$, $NR_{14}(CR_{16}R_{17})_mNR_{12}R_{13}$, $NR_{14}$ $(CR_{16}R_{17})_nSO_2(CR_{18}R_{19})_qR_{11}$, $CONR_{14}(CR_{16}R_{17})_nSO_2$ $(CR_{18}R_{19})_qR_{11}$, $SO_2NR_{14}(CR_{16}R_{17})_nCO(CR_{18}R_{19})_qR_{11}$ and $SO_2NR_{14}(CR_{16}R_{17})_mOR_{11}$.

In the above definitions, $R_{11}$, $R_{14}$, and $R_{15}$, are independently selected from the group consisting of hydrogen, alkyl, substituted alkyl, alkenyl, alkynyl, cycloalkyl, substituted cycloalkyl, C(O)alkyl, C(O)substituted alkyl, C(O)cycloalkyl, C(O) substituted cycloalkyl, C(O)aryl, C(O)substituted aryl, C(O)Oalkyl, C(O)Osubstituted alkyl, C(O) heterocyclo, C(O)heteroaryl, aryl, substituted aryl, heterocyclo and heteroaryl.

Also, $R_{12}$ and $R_{13}$ are herein defined to be independently selected from the group consisting of hydrogen, alkyl, substituted alkyl, cycloalkyl, substituted cycloalkyl, alkenyl, alkynyl, C(O)alkyl, C(O)substituted alkyl, C(O)cycloalkyl, C(O)substituted cycloalkyl, C(O)aryl, C(O)substituted aryl, C(O)Oalkyl, C(O)Osubstituted alkyl, C(O)heterocyclo, C(O)heteroaryl, S(O)$_2$alkyl, S(O)$_2$substituted alkyl, S(O)$_2$cycloalkyl, S(O)$_2$substituted cycloalkyl, S(O)$_2$aryl, S(O)$_2$substituted aryl, S(O)$_2$heterocyclo, S(O)$_2$heteroaryl, aryl, substituted aryl, heterocyclo and heteroaryl, or $R_{12}$ and $R_{13}$ taken together with the nitrogen atom to which they are attached complete a heterocyclo or heteroaryl ring.

$R_{16}$ and $R_{18}$ are herein defined to be independently selected from hydrogen and alkyl or 1 to 4 carbons.

Finally, in the above definitions, $R_{17}$ and $R_{19}$ are independently selected from hydrogen, alkyl of 1 to 4 carbons, and substituted alkyl or 1 to 4 carbons.

n is zero or an integer from 1 to 4.

m is an integer from 2 to 6.

p is an integer from 1 to 3.

q is zero or an integer from 1 to 3.

r is zero or an integer from 1 to 6.

As used herein, the terms $T^1$–$T^{18}$ are defined below:

$T^1$–$T^3$ are independently halo, cyano, nitro, OH, oxo, —OT$^7$, —SH, —ST$^7$, amino, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl.

$T^4$–$T^6$ are each independently,
(1) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, any of which may be optionally independently substituted where valence allows by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —OT$^7$, —SH, —ST$^7$, —C(O)$_r$H, —C(O)$_r$T$^7$, —O—C(O)T$^7$, —SO$_3$H, —S(O)$_t$T$^7$, S(O)$_t$N(T$^8$)T$^7$, -T$^9$-NT$^{11}$T$^{12}$, -T$^9$-N(T$^8$)-T$^{10}$-NT$^{11}$T$^{12}$, -T$^9$-N(T$^{13}$)-T$^{12}$-T$^7$ and -T$^9$-N(T$^{13}$)-T$^{10}$-H; or (2) halo, cyano, nitro, OH, oxo, —OT$^7$, —SH, —ST$^7$, —OT$^7$, —SH, —ST$^7$, —C(O)$_r$H, —C(O)$_r$T$^7$, —O—C(O)T$^7$, —SO$_3$H, —S(O)$_t$T$^7$, S(O)$_t$N(T$^8$)T$^7$, -T$^9$-NT$^{11}$T$^{12}$, -T$^9$-N(T$^8$)-T$^{10}$-NT$^{11}$T$^{12}$, -T$^9$-N(T$^{13}$)-T$^{12}$-T$^7$ or -T$^9$-N(T$^{13}$)-T$^{10}$-H.

The variable t is 1 or 2.

$T^7$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl.

$T^9$ and $T^{10}$ are each independently a single bond, -T$^{14}$-S(O)$_t$-T$^{15}$-, -T$^{14}$-C(O)-T$^{15}$-, -T$^{14}$-C(S)-T$^{18}$-, -T$^{17}$-O-T$^{18}$-, -T$^{17}$-S-T$^{18}$-, -T$^{17}$-O—C(O)-T$^{18}$-, -T$^{17}$-C(O)$_r$T$^{18}$-, -T$^{17}$-C(=NT$^{16}$)-T$^{15}$- or -T$^{14}$-C(O)—C(O)-T$^{15}$-.

The variables $T^8$, $T^{11}$, $T^{12}$, $T^{13}$ and $T^{16}$ are
(1) independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —SH, —ST$^{19}$, —C(O)$_r$H, —C(O)$_r$T$^{19}$, —O—C(O)T$^{19}$ and —S(O)$_r$T$^{19}$; or (2) independently halo, cyano, nitro, OH, oxo, SH, —ST$^{19}$, —C(O)$_r$H, —C(O)$_r$T$^{19}$, —O—C(O)T$^{19}$ or —S(O)$_r$T$^{19}$; or (3) $T^{11}$ and $T^{12}$ may together be alkylene or alkenylene, completing a 3- to 8-membered saturated or unsaturated ring together with the atoms to which they are attached, which ring is substituted with one or more groups listed in the description of $T^{17}$; or (4) $T^{11}$ or $T^{12}$, together with $T^8$, may be alkylene or alkenylene completing a 3- to 8-membered saturated or unsaturated ring together with the nitrogen atoms to which they are attached, which ring is substituted with one or more groups independently selected from $T^{17}$; or (5) $T^{11}$ and $T^{12}$ or $T^8$ and $T^{13}$ together with the nitrogen atom to which they are attached may combine to form a group —N=CT$^{17}$T$^{18}$;

$T^{14}$ and $T^{15}$ are each independently a single bond, alkylene, alkenylene or alkynylene;

$T^{17}$ and $T^{18}$ are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —SH, —ST$^{19}$, —C(O)$_r$H, —C(O)$_r$T$^{19}$, —O—C(O)T$^{19}$ and —S(O)$_r$T$^{19}$; and $T^{19}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl.

The term "optionally substituted" is intended to be synonymous with "unsubstituted or substituted". For example, an optionally substituted heterocycle is equivalent to an unsubstituted or substituted heterocycle.

"T-cell mediated diseases" refers to any disorder or disease state in which modulation of the activity of T-cells is implicated in a process which results in either a pathophysiological state or a process where the normal function of T-cells is intended to be suppressed for therapeutic benefit. Examples of T-cell mediated disorders include transplant rejection, graph verses host disease, and autoimmune disorders, such as rheumatoid arthritis, multiple sclerosis, juvenile diabetes, asthma, and inflammatory bowel disease, T-cell mediated hypersensitivity diseases, ischemic or reperfusion injury, and T-cell proliferative disorders. T-cell mediated diseases are included in the definition of "leukocyte activation-associated disorders" which is defined infra.

The compounds of Formula (I) in accordance with the present invention are employed, typically in the form of a pharmaceutical composition including a pharmaceutically acceptable carrier for the treatment of T-cell mediated disease. The compounds employed for this purpose are typically administered in an amount from about 0.01 to 100 mg/kg/day.

The pharmaceutical compositions comprising at least one compound of Formula (I)may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of Formula (I) may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered in the form of liposomes.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound employed in the present invention may be determined by one of ordinary skill in the art, and includes exemplary dosage amounts for an adult human of from about 0.01 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to inflammatory, immunological, or respiratory cell-associated disorders.

Compounds of Formula (I) include salts, prodrugs and solvates. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the Formula (I) may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pec tinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of Formula (I), or a salt and/or solvate thereof. Solvates of compounds of Formula (I) are preferably hydrates.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, pp. 113–191 (1991); and c) H. Bundgaard, *Advanced Drug Delivery Reviews*, 8, 1–38 (1992), each of which is incorporated herein by reference.

Solvates (e.g., hydrates) of the compounds of Formula (I) are also with the scope of the present invention. Methods of solvation are generally known in the art.

All stereoisomers of the present compounds, such as those which may exist due to asymmetric carbons on the R substituents of the compound of Formula (I), including enantiomeric and diastereomeric forms, are within the scope of this invention. Individual stereoisomers of the compounds of the invention may, for example, be substantially free of other isomers, or may be admixed, for example, as racemates or with all other, or other selected, stereoisomers. The chiral centers of the present invention can have an S or R configuration as defined by the IUPAC 1974 Recommendations.

Preferred Compounds

Preferred compounds within the scope of the present invention include compounds of Formula (I) (above), or pharmaceutically-acceptable salts, solvates or prodrugs thereof, in which the substituent L is

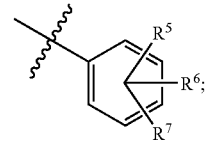

$R^5$, $R^6$ and $R^7$ are
(1) independently selected from H, alkyl, halo, cyano, nitro, OH, SH, aryl, cycloalkyl, heterocyclo and heteroaryl, any of which is optionally independently substituted where valence allows with one to three groups $T^4$, $T^5$ and/or $T^6$; or
(2) —C(O)N($R^8$)($R^9$), S(O)$_t$N($R^8$)($R^9$), —S(O)$_t$$R^{10}$ and C(O)$_t$$R^{10}$.

More preferred compounds of the present invention are selected from Compounds of Formula (II)

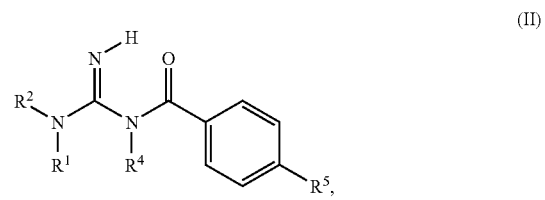

or a pharmaceutically acceptable salt, solvate or prodrug thereof, in which $R^1$, $R^2$ $R^3$ and $R^4$ are defined as in Formula (I) (above);
$R^5$ is halo, cyano, —C(O)N($R^8$)($R^9$), —S(O)$_t$N($R^8$)($R^9$), —C(O)$^t$$R^{10}$ or heteroaryl optionally independently substituted with one to three groups $T^4$, $T^5$ and/or $T^6$.

Within the scope of Formula (II), substituents $R^8$ and $R^9$ preferably are
(1) independently H, alkyl, (cycloalkyl)alkyl or heterocyclo, any of which is optionally independently substituted where valance allows with one to three groups independently selected from $T^4$, $T^5$ and/or $T^6$; or
(2) $R^8$ and $R^9$ may be taken together with the nitrogen atom to which they are attached to form a heterocyclo ring optionally independently substituted with one to three groups independently selected from $T^4$, $T^5$ and/or $T^6$.

Alternatively, preferred compounds of Formula (I) (above), or pharmaceutically-acceptable salts, solvates or prodrugs thereof, are those in which
$R^2$ is

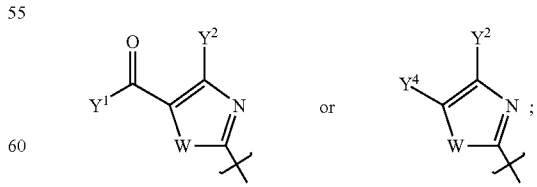

W is O or S (preferably S);
$Y^1$ is —NH$T^{15}$ or OT$^{10}$;
$Y^2$ and $Y^3$ are independently hydrogen, halo, OT$^7$, alkyl or haloalkyl, and $Y^4$ is optionally substituted heteroaryl, cyano, $C(O)_tT^7$ or $S(O)_tNT^{11}T^{12}$.

Also preferred compounds, are those having Formula (III)

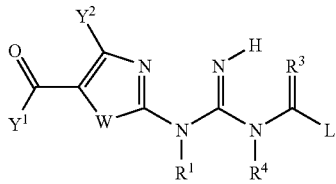

(III)

or pharmaceutically-acceptable salts, solvates or prodrugs thereof, in which

W is O or S;

$Y^1$ is —$NHT^{12}$ or $OT^7$ (preferably $OT^7$, more preferably O $C_{1-4}$ alkyl); and $Y^2$ is alkyl or haloalkyl (preferably alkyl, more preferably $C_{1-4}$ alkyl).

Compounds within the scope of Formula (III), or pharmaceutically acceptable salts, solvates or prodrugs thereof, are more preferred in which L is

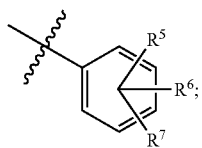

and $R^5$, $R^6$ and $R^7$ are (1) independently selected from H, alkyl, halo, cyano, nitro, OH, SH, aryl, cycloalkyl, heterocyclo and heteroaryl, any of which is optionally independently substituted where valance allows with one to three groups $T^4$, $T^5$ and/or $T^6$; or (2) —$C(O)N(R^8)(R^9)$, $S(O)_tN(R^8)(R^9)$, —$S(O)_tR^{10}$ or $C(O)_tR^{10}$.

Most preferred compounds within the scope of Formula (III), or pharmaceutically-acceptable salts, solvates or prodrugs thereof, are those in which:

L is

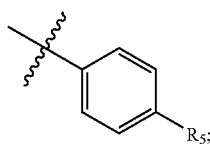

$R^5$ is halo, cyano, —$C(O)N(R^8)(R^9)$, —$S(O)_tN(R^8)(R^9)$, —$C(O)^tR^{10}$ or heteroaryl optionally independently substituted with one to three groups $T^4$, $T^5$ and/or $T^6$; and $R^8$ and $R^9$ are (1) independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which is optionally independently substituted where valance allows with one to three groups independently selected from $T^4$, $T^5$ and/or $T^6$ (preferably H, alkyl, hydroxyalkyl, or heterocyclo, any of which is optionally independently substituted where valance allows with one to three groups selected from $T^4$, $T^5$ and/or $T^6$); or (2) $R^8$ and $R^9$ may be taken together with the nitrogen atom to which they are attached to form a heterocyclo or heteroaryl ring (preferably heterocyclo ring), either of which is optionally independently substituted where valance allows with one to three groups independently selected from $T^4$, $T^5$ and/or $T^6$.

Preferred compounds within the scope of the present invention are those having Formula (IV)

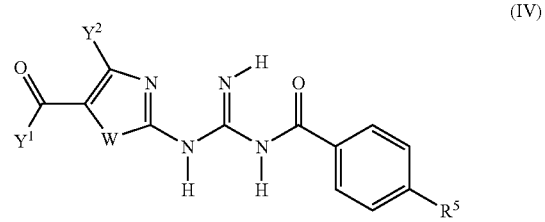

(IV)

or pharmaceutically-acceptable salts, solvates or prodrugs thereof, in which $R^5$ is cyano, —$C(O)N(R^8)(R^9)$ or heteroaryl;

$R^8$ and $R^9$ are (1) independently H, alkyl, hydroxyalkyl, or heterocyclo. any of which is optionally independently substituted where valance allows with one to three groups $T^4$, $T^5$ and/or $T^6$; or (2) $R^8$ and $R^9$ may be taken together with the nitrogen atom to which they are attached to form a heterocyclo which is further optionally independently substituted where valance allows by one to three groups selected from $T^4$, $T^5$ and/or $T^6$;

$Y^1$ is —$NHT^{12}$ or $OT^7$:

$Y^2$ is alkyl or haloalkyl;

$T^4$–$T^6$ are each independently halo, cyano, nitro, OH, oxo, —$OT^7$, —SH, —$ST^7$, amino, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, any of which may be optionally independently substituted where valance allows by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —$OT^7$, —SH, —$ST^7$, —$C(O)_tH$, —$C(O)_tT^7$, —O—$C(O)T^7$, —$SO_3H$, —$S(O)_tT^7$, $S(O)_tN(T^8)T^7$, $-T^9-NT^{11}T^{12}$, $-T^9-N(T^8)-T^{10}-NT^{11}T^{12}$, $-T-N(T^{13})-T^{12}-T^7$ and $-T^9-N(T^{13})-T^{10}-H$;

t is 1 or 2;

$T^7$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^9$ and $T^{10}$ are each independently a single bond, $-T^{14}-S(O)_t-T^{15}-$, $-T^{14}-C(O)-T^{15}-$, $-T^{14}-C(S)-T^{18}-$, $-T^{17}-O-T^{18}-$, $-T^{17}-S-T^{18}-$, $-T^{17}-O-C(O)-T^{18}-$, $-T^{17}-C(O)_tT^{18}-$, $-T^{17}-C(=NT^{16})-T^{15}-$ or $-T^{14}-C(O)-C(O)-T^{15}$;

$T^8$, $T^{11}$, $T^{12}$, $T^{13}$ and $T^{16}$ are (1) independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy) alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —SH, —ST$^7$, —C(O)$_t$H, —C(O)$_t$T$^7$, —O—C(O)T$^7$ and —S(O)$_t$T$^7$; or (2) T$^{11}$ and T$^{12}$ may together be alkylene or alkenylene, completing a 3- to 8-membered saturated or unsaturated ring together with the atoms to which they are attached, which ring is substituted with one or more groups listed in the description of T$^{17}$; or (3) T$^{11}$ or T$^{12}$, together with T$^8$, may be alkylene or alkenylene completing a 3- to 8-membered saturated or unsaturated ring together with the nitrogen atoms to which they are attached, which ring is substituted with one or more groups independently selected from T$^{17}$; or (4) T$^{11}$ and T$^{12}$ or T$^8$ and T$^{13}$ together with the nitrogen atom to which they are attached may combine to form a group —N=CT$^{17}$T$^{18}$;

T$^{14}$ and T$^{15}$ are each independently a single bond, alkylene, alkenylene or alkynylene; and T$^{17}$ and T$^{18}$ are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, or (heteroaryl)alkyl, —SH, —ST$^{10}$, —C(O)$_t$H, —C(O)$_t$T$^{10}$, —O—C(O)T$^{10}$ and —S(O)$_t$T$^{10}$.

More preferable compounds within the scope of Formula (IV), or pharmaceutically-acceptable salts, solvates or prodrugs thereof, are those in which W is S;

Y$^1$ is —OC$_{1-4}$ alkyl; and

Y$^2$ is C$_{1-4}$ alkyl.

Even more preferable compounds of Formula (IV) or pharmaceutically-acceptable salts, solvates or prodrugs thereof, are those in which R$^8$ and R$^9$ are (1) independently H, alkyl, hydroxyalkyl or heterocyclo, any of which is optionally independently substituted where valance allows with one to three groups selected from alkyl, cycloalkyl and oxo; or (2) R$^8$ and R$^9$ may be taken together with the nitrogen atom to which they are attached to form a heterocyclo group optionally substituted with oxo.

Most preferred compounds within the scope of Formula (IV), or pharmaceutically-acceptable salts, solvates or prodrugs thereof, include those in which R$^5$ is selected from:

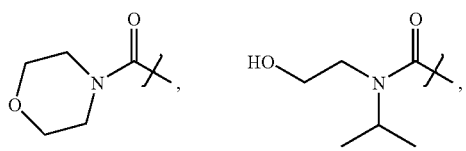

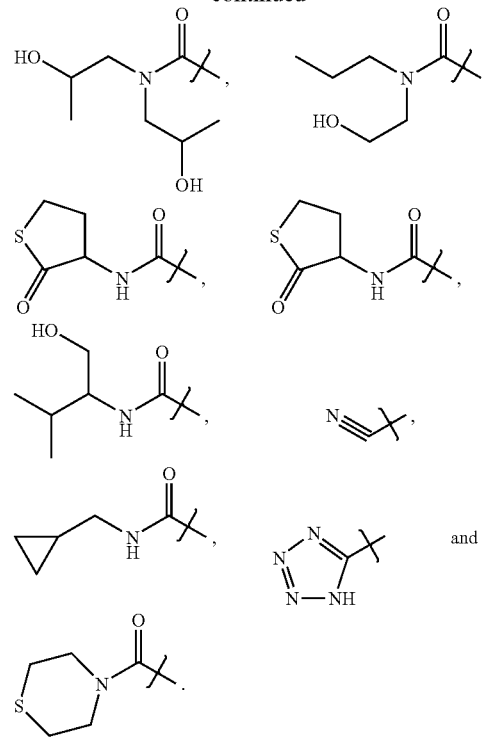

Preferred compounds of Formulas (I), (II), (III) and (IV), or pharmaceutically-acceptable salts, solvates or prodrugs thereof, are those in which R$^1$ and R$^4$ are both H.

Preferred compounds of Formulas (I), (II), (III) or (IV), or pharmaceutically-acceptable salts, solvates or prodrugs thereof, are those in which R$^3$ is O.

Methods of Preparation

Compounds of Formula I may be prepared by reference to the methods illustrated in the following Schemes A through D. As shown therein the end product is a compound having the same structural formula as Formula I. It will be understood that any compound of Formula I may be produced according to Scheme A by the suitable selection of appropriate substitution. Scheme B shows the preparation of amides from compounds of Formula I derived from Scheme A. Scheme C shows the preparation of tetrazoles from compounds of Formula I derived from Scheme A. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined herein or elsewhere in the specification.

Compounds within the scope of the present invention may be prepared by several methods, including condensation of aryl esters with an appropriately substituted guanidine in the presence of a suitable alkoxide base to provide compounds of Formula 1 as illustrated in synthetic Scheme A. For example, guanidine A1 may be heated with diethyl terephthalate in the presence of sodium ethoxide to produce compound A3 which is a compound of Formula I.

Scheme A

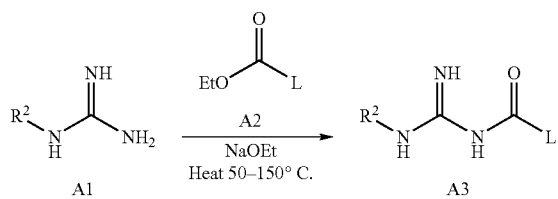

L=aryl, cycloalkyl, heterocyclo, or heteroaryl (optionally substituted)

R²=aryl fused with hetero(cyclo or aryl) bonded through aryl, or heteroaryl (all said ring systems optionally substituted)

Scheme B outlines the conversion of esters of Formula I (depicted in Scheme B where L is phenyl substituted with an ester group; $R^1$ and $R^4$ are H; and $R^3$ is O) to amides of Formula I. Hydrolysis of ester B1 under basic conditions (for instance via lithium hydroxide) affords the acid B2. Coupling of acid B2 under via amide bond coupling techniques (EDC/HOBt) with the appropriately substituted amine, B3, gives the desired amide, B4.

Scheme B

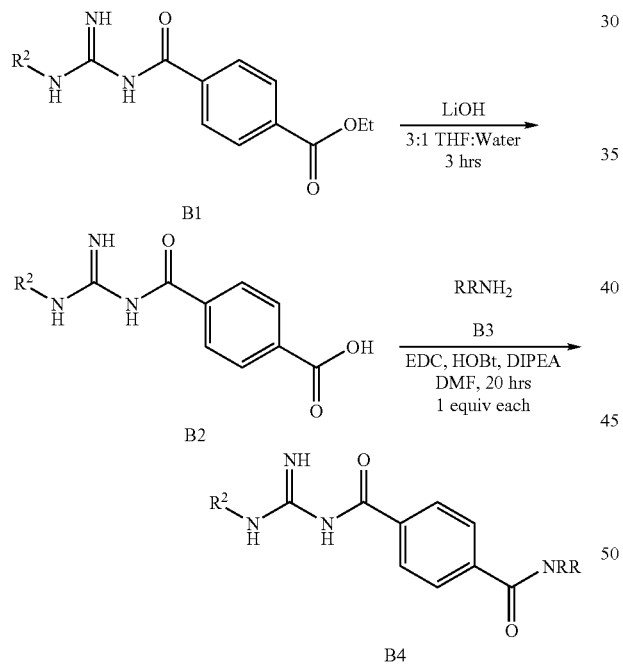

The para-substituted acyl guanidines of structures C1, C2 and C3 (depicted in Scheme C where L is phenyl substituted with a halogen; $R^1$ and $R^4$ are H; and $R^3$ is O) may be prepared as outlined in Scheme A from commercially available reagents or by methods which have been reported in the literature. See e.g., Hallberg, A., et. al., *J. Org. Chem.*, 65, 7984 (2000). Selected methods are outlined in Scheme C. Compound C1 may be prepared via palladium catalyzed cyanation under microwave conditions to yield intermediate C2. Subsequent conversion to the tetrazole, C3, may be accomplished by microwave heating intermediate C2 with ammonium chloride and sodium azide.

Scheme C

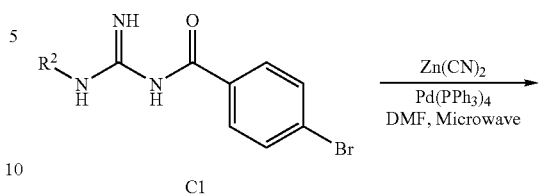

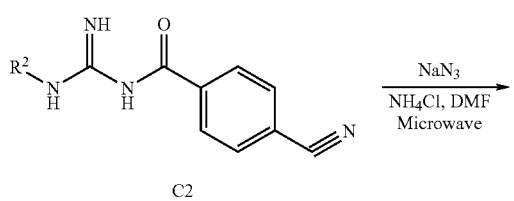

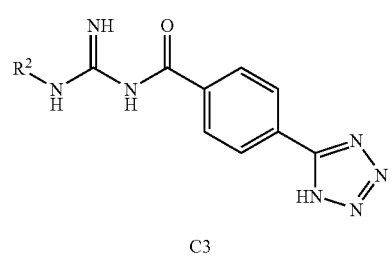

Appropriately substituted guanidines referred to in Scheme A, are either commercially available or may be readily prepared by a number of methods known to one skilled in the art of organic chemistry. For example, as illustrated in Scheme D, where it is desirable to obtain a thienyl group in the $R^2$ position, alpha-haloketone D1 may be reacted with thiobiuret, D2, to provide the guanidine salt D3. D3 is then liberated from its corresponding salt by treatment with a basic resin, sodium hydroxide, sodium methoxide, or an amine base to provide intermediate D4. D4 can be further elaborated as described in Scheme A to provide compounds of Formula I.

Scheme D

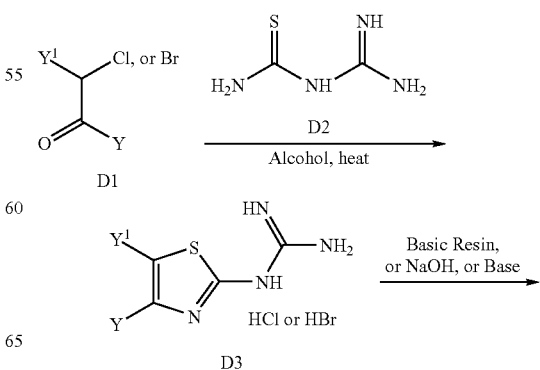

-continued

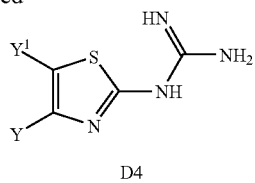

D4

Utility

The compounds of Formula (I), are useful in the treatment (including prevention, partial alleviation or cure) of leukocyte activation-associated disorders. These disorders include (but are not limited to) transplant rejection (such as organ transplant, acute transplant, xenotransplant or heterograft or homograft such as is employed in burn treatment); protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to asthma, exercise induced asthma, chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell-mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (e.g., asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea.

The term "leukocyte activation-associated disorder" or "leukocyte activation-mediated disorder" as used herein includes each of the above referenced diseases or disorders. The compounds of the present invention are useful for treating the aforementioned exemplary disorders irrespective of their etiology.

The present invention thus provides methods for the treatment of leukocyte activation-associated disorders (discussed above) comprising the step of administering to a subject in need thereof of at least one compounds of Formula (I). Other therapeutic agents such as those described below may be employed with the compounds of the present invention. In the methods of the present invention, such other therapeutic agent(s) may be administered prior to, simultaneously with or following the administration of the compound(s) of the present invention.

The methods of treating diseases which would benefit from administering compounds of Formula (I) alone or in combination with each other and/or other suitable therapeutic agents useful in treating such conditions. These agents include, without limitation: immunosuppressants such as cyclosporins (e.g., cyciosporin A), anti-IL-1 agents, such as Anakinra®, the IL-1 receptor antagonist, CTLA4-Ig, antibodies such as anti-ICAM-3, anti-IL-2 receptor (Anti-Tac®), anti-CD45RB, anti-CD2, anti-CD3, anti-CD4. anti-CD80, anti-CD86, monoclonal antibody OKT3, agents blocking the interaction between CD40 and CD154, such as antibodies specific for CD40 and/or CD 154 (i.e., CD40L), fusion proteins constructed from CD40 and CD154 (CD40Ig and CD8–CD154), interferon beta, interferon gamma, methotrexate, FK506 (tacrolimus, Prograf®), rapamycin (sirolimus or Rapamune®)mycophenolate mofetil, leflunomide (Arava®), azathioprine and cyclophosphamide, inhibitors, such as nuclear translocation inhibitors, of NF-kappa B function, such as deoxyspelgualin (DSG), non-steroidal antiinflammatory drugs (NSAIDs) such as ibuprofen, cyclooxygenase-2 (COX-2) inhibitors such as celecoxib (Celebrex®) and rofecoxib (Vioxx®), or derivatives thereof, steroids such as prednisone or dexamethasone, gold compounds TNF-α inhibitors such as tenidap, anti-TNF antibodies or soluble TNF receptor such as etanercept (Enbrel®), inhibitors of p-38 kinase such as BIRB-796, RO-3201,195, VX-850, and VX-750, beta-2 agonists such as albuterol, levalbuterol (Xopenex®), and salmeterol (Serevent®), inhibitors of leukotriene synthesis such as montelukast (Singulair®) and zarifluklast (Accolate®), and anticholinergic agents such as ipratropium bromide (Atrovent®), PDE4 inhibitors such as Arofyline, Cilomilast, Roflumilast, C-11294A, CDC-801, BAY-19-8004, Cipamfylline, SCH351591, YM-976, PD-189659, Mesiopram, Pumafentrine, CDC-998, IC-485, and KW-4490, and PDE7 inhibitors such as IC242. See Lee, et al., *Cell Signalling*, 14, 277–284, (2002). Other compounds which may be used in combination with compounds of Fomula (I) to treat diseases are disclosed in the following patent documents: WO 0068230, WO 0129049, WO 0132618, WO 0134601, WO 0136425, WO 0174786, WO 0198274, WO 0228847; U.S. Prov. Appl. Ser. Nos. 60/287,964, and 60/355,141; as well as anti-cytokines such as anti-IL-1 mAb or IL-1 receptor agonist; anti-IL-4 or IL-4 receptor fusion proteins; and PTK inhibitors such as those disclosed in U.S. Pat. Nos. 5,990, 109, 6,235,740 and 6,239,133, U.S. Appl. Ser. No. 60/065, 042 and. Ser. No. 09/173,413, filed Nov. 10, 1997 and Oct. 15, 1998, respectively. All of the foregoing patents and patent applications are incorporated herein by reference in their entirety.

See also the following documents and references cited therein: Hollenbaugh, D., et al., *J. Immunol. Methods*, 188(1), 1–7 (1995); Hollenbaugh, D., et al., *EMBO J.*, 11(12),4313–4321 (1992); and Moreland, L. W., et al., *New England J. of Medicine*, 337(3), 141–147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

Use of the compounds having Formula (I) of the present invention in treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to asthma, exercise induced asthma, chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea.

The combined activity of the present compounds towards T-cells may be of value in the treatment of any of the aforementioned disorders.

In a particular embodiment, the compounds of the present invention are useful for the treatment of the aforementioned exemplary disorders irrespective of their etiology, for example, in the treatment of transplant rejection, rheumatoid arthritis, multiple sclerosis, chronic obstructive pulmonary disease, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, respiratory diseases such as asthma, COPD and bronchitis or atopic dermatitis.

T-Cell Proliferation Assay

Peripheral blood mononuclear cells (PBMC) were isolated from whole blood by density gradient centrifugation over Lymphoprep, 1.077. Cells were plated into 96 well U-bottom plates at $2.5 \times 10_5$ cells/well in 10% FBS RPMI 1640 (Life Technologies/Gibco-BRL) containing 10 ug/ml anti-CD3 (G19-4, Bristol-Myers Squibb P.R.I., Princeton, N.J.) and 1 ug/ml anti-CD28 (9.3, Bristol-Myers Squibb P.R.I.) in the presence and absence of inhibitors. DMSO (used as a solvent for inhibitors) was added to the medium at 0.1% final concentration. The total volume per well was 200 µL. Cells were incubated at 37 C 5% CO2 for 3 days, at which time 0.5 µCi of $^3$H-thymidine was added to each well. Six hours following the addition of $^3$H-thmidine, the plates were harvested onto filter plates, 30 ul EcoLite scintillant (ICN, Costa Mesa, Calif.) was added per well, and plates read on a Top Count-NXT scintillation counter.

TNFα Secretion Assay

The ability of compounds to inhibit the production and secretion of TNFα from leukocytes was performed using either PBMC (obtained as described above) or the THP-1 cell line as a source of monocytes. Compounds were diluted in RPMI 1640 supplemented with 10% FBS and DMSO at a final concentration of 0.2%. Cells ($2 \times 10^5$/well in U-bottom 96 well plates) were pre-incubated with compounds for 30 min at 37 C prior to addition of lipopolysaccharide (LPS) at a final concentration of 6.25 ng/ml in a total volume of 200 µL. After 4 h at 37° C., 50 µL of supernatant was carefully aspirated for detection of soluble TNFα. Soluble TNFα was detected by ELISA developed by R&D Systems (Minneapolis, Minn.) according to the manufacturer's instructions.

EXAMPLES

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "A1.1" denotes the title compound of step 1 of Example A1), or by the example only where the compound is the title compound of the example (for example, "A2" denotes the title compound of Example A2).

| | Abbreviations |
|---|---|
| Ac | Acetyl |
| AcOH | Acetic acid |
| aq. | Aqueous |
| CDI | Carbonyldiimidazole |
| Bn | Benzyl |
| Bu | Butyl |
| Boc | tert-butoxycarbonyl |
| DMAP | Dimethylaminopyridine |
| DMA | N,N-Dimethylacetamide |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| H | Hydrogen |
| h | Hours |
| i | iso |
| HPLC | High pressure liquid chromatography |
| HOAc | Acetic acid |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| M$^+$ | (M + H)$^+$ |
| M$^{+1}$ | (M + H)$^+$ |
| MS | Mass spectrometry |
| n | normal |
| Pd/C | Palladium on carbon |
| Ph | Phenyl |
| Pr | Propyl |
| Ret Time | Retention time |
| rt or RT | Room temperature |
| sat. | Saturated |
| S-Tol-BINAP | (S)-(−)-2,2'-Bis(di-p-tolylphosphino)-1,1'-binapthyl |
| t | tert |
| TFA | Trifluoroacetic acid |
| THF | Tetrahydrofuran |
| YMC | YMC Inc, Wilmington, NC 28403 |

Example A1

4-Methyl-2-{N'-[4-(thiomorpholine-4-carbonyl)-benzoyl]-guanidino}-thiazole-5-carboxylic acid ethyl ester

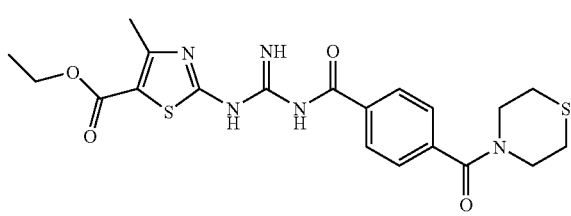

A1

A1.1

2-[(Aminoiminomethyl)amino]-4-methyl-5-thiazole-carboxylic acid ethyl ester

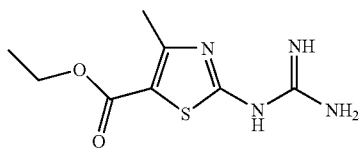

A1.1

A solution of 2-imino-4-thiobiuret (20.0 g, 0.17 mol), 2-chloroacetoacetate (28 g, 0.17 mol) in ethanol (500 mL) was heated to 100° C. for 4 hours. The reaction mixture was concentrated to half volume and poured into 1 liter of 1N NaOH. The white solid which precipitated out was collected by filtration and dried under vacuum to yield A1.1 (30.5 g, 79%). $^1$H-NMR (DMSO-$d_6$) δ: 4.22 (2H, q, J=7 Hz ), 2.50 (3H, merge with DMSO), 1.26 (3H, t, J=7 Hz ). HPLC: 97.7%, ret. time=1.619 min., LC/MS (M+H)$^+$=229.

A1.2

2-[N'-(4-Ethoxycarbonyl-benzoyl)-guanidino]-4-methyl-thiazole-5-carboxylic acid ethyl ester

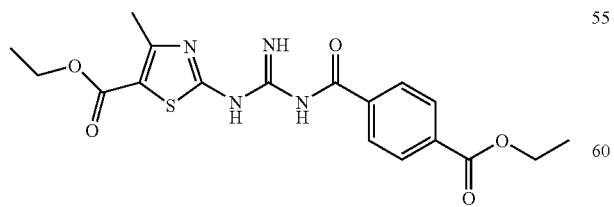

A1.2

Sodium (1.1 g, 46.0 mmol) was added in one portion to dry ethanol (50 ml) under a nitrogen atmosphere. After complete consumption of the sodium, A1.1 (3.0 g, 13.0 mmol) was added in one portion and the resulting suspension stirred at room temperature for 30 min. Diethyl terephthalate (3.2 g, 14.3 mmol) was then added dropwise over 5 min. and the reaction mixture was heated to 120 to 130° C. overnight. The reaction mixture was allowed to cool to room temperature and poured onto water (50 ml), followed by extraction with ethyl acetate (3×60 ml). The combined organics were dried (MgSO$_4$) and evaporated in vacuo to yield A1.2 (1.37 g, 26%). $^1$H-NMR (DMSO-$d_6$) δ: 8.10–8.06 (4H, m), 4.36 (2H, q, J=8 Hz ), 4.23 (2H, q, J=8 Hz), 2.56 (3H, s,), 1.35 (3H, t, J=8 Hz), 1.30–1.20 (3H, m). HPLC: 95%, ret. time=2.037 min., LC/MS (M+H)$^+$=406.17.

A1.3

2-[N'-(4-Carboxy-benzoyl)-guanidino]-4-methyl-thiazole-5-carboxylic acid ethyl ester

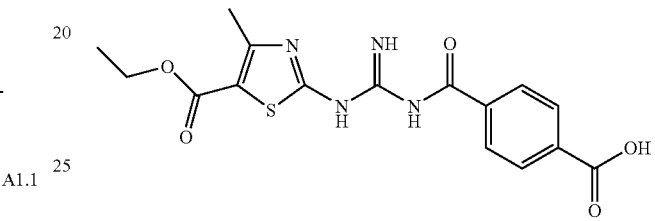

A1.3

Lithium hydroxide hydrate (5 mg, 0.12 mmol) was added in one portion to a solution of A1.2 (40 mg, 0.99 mmol) in 3:1 THF:H$_2$O (1 ml) and the reaction mixture was allowed to stir at room temperature for 12 hours. The reaction mixture was acidified with 1N hydrochloric acid (2 ml) and the resulting solution extracted with ethyl acetate (3×5 ml). The combined organics were dried (MgSO$_4$) and evaporated in vacuo. The crude acid was purified by column chromatography using 10:1 EtOAc:MeOH as eluent to yield A1.3 (4.4mg, 12%) as a white solid. $^1$H-NMR (CD$_3$OD) δ: 8.00–7.89 (4H, m), 4.18 (2H, q, J=7.8 Hz), 2.50 (3H, s,), 1.24 (3H, t, J=7.8 Hz). HPLC: 95%, ret. time=1.797 min., LC/MS (M+H)$^+$=377.02.

A1.4

4-Methyl-2-{N'-[4-(thiomorpholine-4-carbonyl)-benzoyl]-guanidino}-thiazole-5-carboxylic acid ethyl ester To a solution of A1.3 (70 mg, 0.19 mmol) in DMF (2 mL) was added thiomorpholine (29 mg, 0.28 mmol), EDC (71 mg, 0.37 mmol), HOBt (50 mg, 0.37 mmol) and DIPEA (0.1 ml, 0.56 mmol). The resulting solution was allowed to stir at room temperature overnight under a nitrogen atmosphere. The reaction mixture was quenched by the addition of saturated sodium bicarbonate solution (2 ml) and the aqueous was extracted with ethyl acetate (3×10 ml). The combined organics were dried (MgSO$_4$) and evaporated in vacuo. The crude product was purified with prep. HPLC (reverse phase) to yield A1(38 mg, 43%). HPLC: 98%, ret. time=1.797 min., LC/MS (M+H)$^+$=462.14.

Example A2–A10

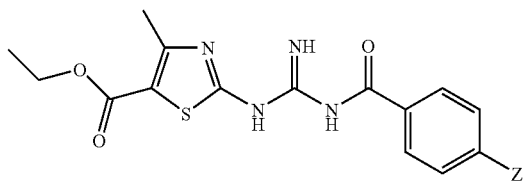

Examples A2–A8 were prepared in a similar manner to that used for Example A1. Example A9 was prepared in a similar manner to A1 except the intermediate A1.1 was reacted with commercially available ethyl-4-bromobenzoate. The cyano- and tetrazole-groups were installed as described in synthetic scheme C.

TABLE A1

| Ex. | Z | Name | HPLC Retention (min) | MS Reported |
|---|---|---|---|---|
| A2 |  | 4-Methyl-2-{N'-[4-(morpholine-4-carbonyl)-benzoyl]-guanidino}-thiazole-5-carboxylic acid ethyl ester | 1.627 | 446.17 |
| A3 |  | 2-(N'-{4-[(2-Hydroxy-ethyl)-isopropyl-carbamoyl]-benzoyl}-guanidino)-4-methyl-thiazole-5-carboxylic acid ethyl ester | 1.513 | 461.16 |
| A4 |  | 2-(N'-{4-[Bis-(2-hydroxy-propyl)-carbamoyl]-benzoyl}-guanidino)-4-methyl-thiazole-5-carboxylic acid ethyl ester | 1.643 | 492.13 |
| A5 |  | 2-(N'-{4-[(2-Hydroxy-ethyl)-propyl-carbamoyl]-benzoyl}-guanidino)-4-methyl-thiazole-5-carboxylic acid ethyl ester | 1.503 | 461.13 |
| A6 |  | 4-Methyl-2-{N'-[4-(2-oxo-tetrahydro-thiophen-3-ylcarbamoyl)-benzoyl]-guanidino}-thiazole-5-carboxylic acid ethyl ester | 1.687 | 476.11 |
| A7 |  | 2-[N'-(4-Cyclopropylcarbamoyl-benzoyl)-guanidino]-4-methyl-thiazole-5-carboxylic acid ethyl ester | 1.823 | 430.15 |
| A8 |  | 2-{N'-[4-(1-Hydroxy-2-methyl-propylcarbamoyl)-benzoyl]-guanidino}-4-methyl-thiazole-5-carboxylic acid ethyl ester | 1.793 | 462.19 |
| A9 |  | 2-[N'-(4-Cyano-benzoyl)-guanidino]-4-methyl-thiazole-5-carboxylic acid ethyl ester | 1.837 | 358.01 |
| A10 |  | 4-Methyl-2-{N'-[4-(1H-tetrazol-5-yl)-benzoyl]-guanidino}-thiazole-5-carboxylic acid ethyl ester | 1.757 | 401.03 |

[a]HPLC conditions used to determine retention times; 2 min gradient 0–100% B in A (A; 0.1% TFA in 90/10 water/methanol; B; 0.1% TFA in 10/90 water/methanol) using a Phenomenex S5 ® column at 254 nm.

We claim:
1. A compound of Formula I

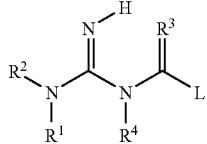

or an enantiomer, diastereomer or a pharmaceutically-acceptable salt thereof,
wherein:
$R^1$ and $R^4$ are independently hydrogen or alkyl optionally independently substituted where valence allows with one to three groups, $T^1$, $T^2$, and/or $T^3$;
$R^2$ is

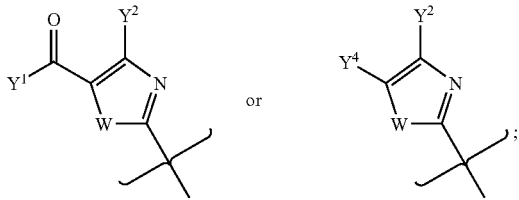

W is O or S;
$Y^1$ is —$NHT^{12}$ or $OT^7$;
$Y^2$ is hydrogen, halo, $OT^7$ alkyl, haloalkyl;
$Y^4$ is optionally substituted heteroaryl, cyano, $C(O)_tT^7$ or $S(O)_tNT^{11}T^{12}$;
$R^3$ is O, S, NH;
L is

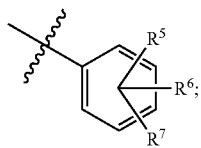

$R^5$, $R^6$ and $R^7$ are independently selected from (i)H, alkyl, halo, cyano, nitro, OH, SH, aryl, cycloalkyl, heterocyclo and heteroaryl, any of which is optionally independently substituted where valence allows with one to three groups $T^4$, $T^5$, and/or $T^6$; or (ii) —C(O)N($R^8$)($R^9$), S(O)$_t$N($R^8$)($R^9$), —S(O)$_tR^{10}$, or C(O)$_tR^{10}$;
$R^8$ and $R^9$ are
(1) independently H, alkyl, alkenyl, aryl, (aryl)alkyl, heteroaryl, (heteroaryl)alkyl, cycloalkyl, (cycloalkyl)alkyl, heterocyclo, or (heterocyclo)alkyl, any of which is optionally independently substituted where valance allows with one to three groups independently selected from $T^4$, $T^5$, and/or $T^6$; or
(2) $R^8$ and $R^9$ may be taken together with the nitrogen atom to which they are attached to form a heterocyclo or heteroaryl ring, either of which is optionally independently substituted where valance allows with one to three groups independently selected from $T^4$, $T^5$, and/or $T^6$;

$R^{10}$ is H, alkyl or substituted alkyl;
$T^1$–$T^3$ are each independently halo, cyano, nitro, OH, oxo, —$OT^7$, —SH, —$ST^7$, amino, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
$T^4$–$T^6$ are each independently
(1) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted where valence allows by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —$OT^7$, —SH, —$ST^7$, —$C(O)_tH$, —$C(O)_tT^7$, —O—$C(O)T^7$, —$SO_3H$, —$S(O)_tT^7$, $S(O)_tN(T^8)T^7$, -$T^9$-$NT^{11}T^{12}$, -$T^9$-$N(T^8)$-$T^{10}$-$NT^{11}T^{12}$-, -$T^9$-$N(T^{13})$-$T^{12}$-$T^7$, and -$T^9$-$N(T^{13})$-$T^{10}$-H; or
(2) halo, cyano, nitro, OH, oxo, —$OT^7$, —SH, —$ST^7$, —$OT^7$, —SH, —$ST^7$, —$C(O)_tH$, —O—$C(O)T^7$, —O—$C(O)T^7$, —$SO_3H$, —$S(O)_tT^7$, $S(O)_tN(T^8)T^7$, -$T^9$-$NT^{11}T^{12}$, -$T^9$-$N(T^8)$-$T^{10}$-$NT^{11}T^{12}$, -$T^9$-$N(T^{13})$-$T^{12}$-$T^7$ or -$T^9$-$N(T^{13})$-$T^{10}$-H;
t is 1 or 2;
$T^7$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
$T^9$ and $T^{10}$ are each independently a single bond, -$T^{14}$-S(O)$_t$-$T^{15}$-, -$T^{14}$-C(O)-$T^{15}$-, -$T^{14}$-C(S)-$T^{18}$-, -$T^{17}$-O-$T^{18}$-, -$T^{17}$-S-$T^{18}$-, -$T^{17}$-O—C(O)-$T^{18}$-, -$T^{17}$-C(O)$_tT^{18}$-, -$T^{17}$-C(=$NT^{16}$)-$T^{15}$-, or -$T^{14}$-C(O)—C(O)-$T^{15}$-;
$T^8$, $T^{11}$, $T^{12}$, $T^{13}$ and $T^{16}$ are
(1) independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —SH, —$ST^{19}$, —$C(O)_tH$, —$C(O)_tT^{19}$, —O—$C(O)T^{19}$, and —$S(O)_tT^{19}$; or
(2) independently halo, cyano, nitro, OH, oxo, SH, —$ST^{19}$, —$C(O)_tH$, —$C(O)_tT^{19}$, —O—$C(O)T^{19}$, or —$S(O)_tT^{19}$; or
(3) $T^{11}$ and $T^{12}$ may together be alkylene or alkenylene, completing a 3- to 8-membered saturated or unsaturated ring together with the atoms to which they are attached, which ring is substituted with one or more groups listed in the description of $T^{17}$; or
(4) $T^{11}$ or $T^{12}$ together with $T^8$, may be alkylene or alkenylene completing a 3- to 8-membered saturated or unsaturated ring together with the nitrogen atoms to which they are attached, which ring is substituted with one or more groups independently selected from $T^{17}$; or (5) $T^{11}$ and $T^{12}$ or $T^8$ and $T^{13}$ together with the nitrogen atom to which they are attached may combine to form a group —N=$CT^{17}T^{18}$;

$T^{14}$ and $T^{15}$ are each independently a single bond, alkylene, alkenylene, or alkynylene;

$T^{17}$ and $T^{18}$ are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —SH, —$ST^{19}$, —$C(O)_tH$, —$C(O)_tT^{19}$, —O—$C(O)T^{19}$, and —$S(O)_tT^{19}$; and $T^{19}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl.

2. The compound of claim 1 having Formula (II)

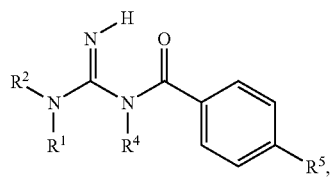

(II)

or an enantiomer, diastereomer or a pharmaceutically-acceptable salt, thereof, wherein;

$R^5$ is heteroaryl optionally independently substituted with one to three groups $T^4$, $T^5$, and/or $T^6$, halo, cyano, —C(O)N($R^8$)($R^9$), —S(O)$_t$N($R^8$)($R^9$), or —C(O)$_tR^{10}$;

$R^8$ and $R^9$ are (1) independently H, alkyl, (cycloalkyl)alkyl, or heterocyclo, any of which is optionally independently substituted where valance allows with one to three groups independently selected from $T^4$, $T^5$, and/or $T^6$; or (2) $R^8$ and $R^9$ may be taken together with the nitrogen atom to which they are attached to form a heterocyclo ring optionally independently substituted with one to three groups independently selected from $T^4$, $T^5$, and/or $T^6$.

3. A compound of claim 1, or an enantiomer, diastereomer or a pharmaceutically-acceptable salt thereof, wherein:

$R^2$ is

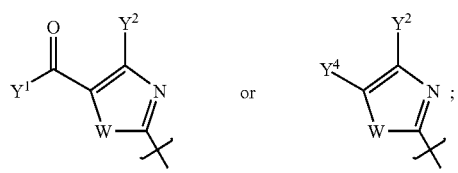

W is O or S;

$Y^1$ is —$NHT^{15}$ or $OT^{10}$;

$Y^2$ and $Y^3$ are independently hydrogen, halo, $OT^7$, alkyl, or haloalkyl; and $Y^4$ is optionally substituted heteroaryl, cyano, C(O)$_tT^7$, or S(O)$_tNT^{11}T^{12}$.

4. A compound of claim 3, having Formula (III)

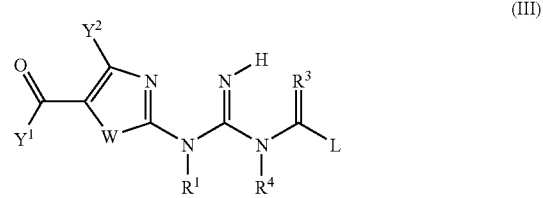

(III)

or an enantiomer, diastereomer or a pharmaceutically-acceptable salt, thereof, wherein:

W is O or S;

$Y^1$ is —$NHT^{12}$ or $OT^{10}$; and $Y^2$ is alkyl or haloalkyl.

5. A compound of claim 4, or an enantiomer, diastereomer or a pharmaceutically-acceptable salt thereof, wherein:

$Y^1$ is —$OC_{1-4}$ alkyl; and $Y^2$ is $C_{1-4}$ alkyl.

6. A compound of claim 5, or an enantiomer, diastereomer or a pharmaceutically-acceptable salt thereof, wherein:

$R^5$ is halo, cyano, —C(O)N($R^8$)($R^9$), —S(O)$_t$N($R^8$)($R^9$), —C(O)$_tR^{10}$, or heteroaryl optionally independently substituted with one to three groups $T^4$, $T^5$, and/or $T^6$; and $R^8$ and $R^9$ are (1) independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which is optionally independently substituted where valance allows with one to three groups independently selected from $T^4$, $T^5$, and/or $T^6$; or (2) $R^8$ and $R^9$ may be taken together with the nitrogen atom to which they are attached to form a heterocyclo or heteroaryl ring, either of which is optionally independently substituted where valance allows with one to three groups independently selected from $T^4$, $T^5$, and/or $T^6$.

7. A compound of claim 6, or an enantiomer, diastereomer, or a pharmaceutically-acceptable salt thereof, wherein:

$R^8$ and $R^9$ are (1) independently H, alkyl, hydroxyalkyl or heterocyclo, any of which is optionally independently substituted where valance allows with one to three groups selected from $T^4$, $T^5$, and/or $T^6$; or (2) $R^8$ and $R^9$ may be taken together with the nitrogen atom to which they are attached to form a heterocyclo which is further optionally independently substituted where valence allows by one to three groups selected from $T^4$, $T^5$, and/or $T^6$.

8. A compound of Formula (IV)

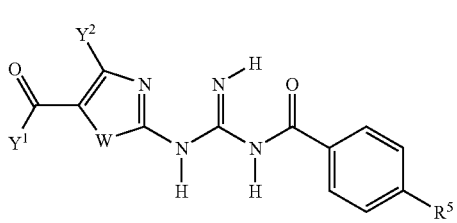

or an enantiomer, diastereomer, or an and pharmaceutically-acceptable salt thereof, wherein:
$R^5$ is cyano, —C(O)N($R^8$)($R^9$) or heteroaryl;
$R^8$ and $R^9$ are
  (1) independently H, alkyl, hydroxyalkyl, or heterocyclo, any of which is optionally independently substituted where valance allows with one to three groups $T^4$, $T^5$, and/or $T^6$; or
  (2) $R^8$ and $R^9$ may be taken together with the nitrogen atom to which they are attached to form a heterocyclo which is further optionally independently substituted where valence allows by one to three groups selected from $T^4$, $T^5$, and/or $T^6$;
$Y^1$ is —NH$T^{12}$ or O$T^7$;
$Y^2$ is alkyl or haloalkyl;
$T^4$–$T^6$ are each independently
  (1) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted where valence allows by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —O$T^7$, —SH, —S$T^7$, —C(O)$_t$H, —C(O)$_t T^7$, —O—C(O)$T^7$, —SO$_3$H, —S(O)$_t T^7$, S(O)$_t$N($T^8$)$T^7$, -$T^9$-N$T^{11}T^{12}$, -$T^9$-N($T^8$)-$T^{10}$-N$T^{11}T^{12}$,-$T^9$-N($T^{13}$)-$T^{12}$-$T^7$, and -$T^9$-N($T^{13}$)-$T^{10}$-H; or
  (2) halo, cyano, nitro, OH, oxo, —O$T^7$, —SH, —S$T^7$, —O$T^7$, —SH, —S$T^7$, —C(O)$_t$H, —C(O)$_t T^7$, —O—C(O)$T^7$, —SO$_3$H, —S(O)$_t T^7$, S(O)$_t$N($T^8$)$T^7$, -$T^9$-N$T^{11}T^{12}$, -$T^9$-N($T^8$)-$T^{10}$-N$T^{11}T^{12}$, -$T^9$-N($T^{13}$)-$T^{12}$-$T^7$, or -$T^9$-N($T^{13}$)-$T^{10}$-H;
t is 1 or 2;
$T^7$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
$T^9$ and $T^{10}$ are each independently a single bond, -$T^{14}$-S(O)$_t$-$T^{15}$-, -$T^{14}$-C(O)-$T^{15}$-, -$T^{14}$-C(S)-$T^{18}$-, -$T^{17}$-O-$T^{18}$-, -$T^{17}$-S-$T^{18}$-, -$T^{17}$-O—C(O)-$T^{18}$-, -$T^{17}$-C(O)$_t T^{18}$-, -$T^{17}$-C(=N$T^{16}$)-$T^{15}$-, or -$T^{14}$-C(O)—C(O)-$T^{15}$-;
$T^8$, $T^{11}$, $T^{12}$, $T^{13}$, and $T^{16}$ are
  (1) independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —SH, —S$T^{19}$, —C(O)$_t$H, —C(O)$_t T^{19}$, —O—C(O)$T^{19}$, and —S(O)$_t T^{19}$; or
  (2) independently halo, cyano, nitro, OH, oxo, SH, —S$T^{19}$, —C(O)$_t$H, —C(O)$_t T^{19}$, —O—C(O)$T^{19}$, or —S(O)$_t T^{19}$; or
  (3) $T^{11}$ and $T^{12}$ may together be alkylene or alkenylene, completing a 3- to 8-membered saturated or unsaturated ring together with the atoms to which they are attached, which ring is substituted with one or more groups listed in the description of $T^{17}$; or
  (4) $T^{11}$ or $T^{12}$, together with $T^8$, may be alkylene or alkenylene completing a 3- to 8-membered saturated or unsaturated ring together with the nitrogen atoms to which they are attached, which ring is substituted with one or more groups independently selected from $T^{17}$; or
  (5) $T^{11}$ and $T^{12}$ or $T^8$ and $T^{13}$ together with the nitrogen atom to which they are attached may combine to form a group —N=C$T^{17}T^{18}$;
$T^{14}$ and $T^{15}$ are each independently a single bond, alkylene, alkenylene, or alkynylene;
$T^{17}$ and $T^{18}$ are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyo)alkyl, heteroaryl, (heteroaryl)alkyl, —SH, —S$T^{19}$, —C(O)$_t$H, —C(O)$_t T^{19}$, —O—C(O)$T^{19}$, and —S(O)$_t T^{19}$; and
$T^{19}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl.

9. A compound of claim 8, or an enantiomer, diastereomer or a pharmaceutically-acceptable salt thereof, wherein
W is S;
$Y^1$ is —O$C_{1-4}$ alkyl: and
$Y^2$ is $C_{1-4}$ alkyl.

10. A compound of claim 9, or an enantiomer, diastereomer or a pharmaceutically-acceptable salt thereof, wherein:
$R^8$ and $R^9$ are
  (1) independently H, alkyl, hydroxyalkyl, or heterocyclo, any of which is optionally independently substituted where valance allows with one to three groups selected from alkyl, cycloalkyl, and oxo; or
  (2) $R^8$ and $R^9$ may be taken together with the nitrogen atom to which they are attached to form a heterocyclo group optionally substituted with oxo.

11. A compound of claim 10, or an enantiomer, diastereomer or a pharmaceutically-acceptable salt thereof, wherein $R^5$ is selected from:

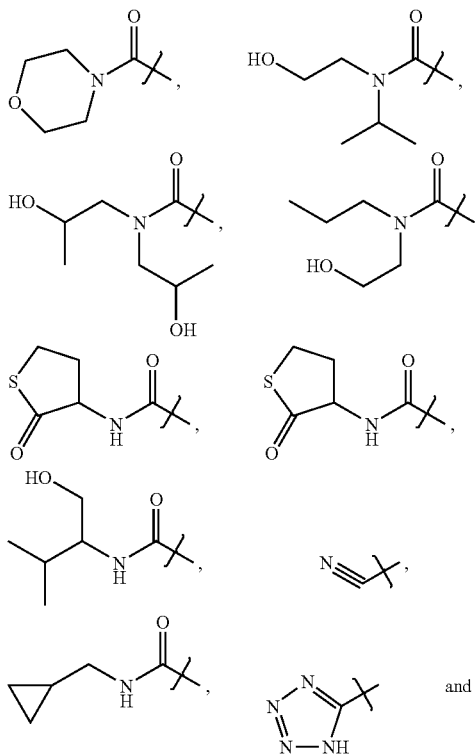

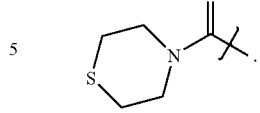

12. A compound of claim 1, or an enantiomer, diastereomer or a pharmaceutically-acceptable salt thereof, wherein $R^1$ and $R^4$ are both H.

13. A compound of claim 1, or an enantiomer, diastereomer or a pharmaceutically-acceptable salt thereof, wherein $R^3$ is O.

14. A pharmaceutical composition comprising one or more compounds of claim 1 and a pharmaceutically acceptable carrier.

15. A pharmaceutical composition of claim 14 further comprising at least one additional therapeutic agent selected from PDE4 inhibitors, consisting of NSAIDs, COX-2 inhibitors, TNF-α inhibitors, beta-2 agonists, anti-cholinergic agents, and steroids.

16. A method of treating a leukocyte activation-associated disorder wherein the disorder is rheumatoid arthritis which comprises administering an effective amount of one or more compounds of claim 1 to a patient in need thereof.

* * * * *